US008086306B2

(12) United States Patent
Katzman et al.

(10) Patent No.: US 8,086,306 B2
(45) Date of Patent: Dec. 27, 2011

(54) OTC AUTOMATIC EXTERNAL DEFIBRILLATOR WITH QUICK INSTALL BATTERY

(75) Inventors: Wendy Katzman, Seattle, WA (US); Jesse Warwick, Shoreline, WA (US); Dan Powers, Issaquah, WA (US); Hans Griesser, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 717 days.

(21) Appl. No.: 11/722,209

(22) PCT Filed: Dec. 20, 2005

(86) PCT No.: PCT/IB2005/054341
§ 371 (c)(1),
(2), (4) Date: Jun. 20, 2007

(87) PCT Pub. No.: WO2006/070313
PCT Pub. Date: Jul. 6, 2006

(65) Prior Publication Data
US 2009/0281585 A1      Nov. 12, 2009

Related U.S. Application Data

(60) Provisional application No. 60/639,476, filed on Dec. 27, 2004, provisional application No. 60/689,115, filed on Jun. 8, 2005.

(51) Int. Cl.
*A61N 1/39*      (2006.01)

(52) U.S. Cl. ............................................. 607/5; 607/8
(58) Field of Classification Search ................. 607/5, 6, 607/7, 8; 434/265; 128/696
See application file for complete search history.

(56) References Cited

U.S. PATENT DOCUMENTS

| 4,610,254 A * | 9/1986 | Morgan et al. ..................... 607/6 |
| 4,619,265 A | 10/1986 | Morgan et al. |
| 5,658,316 A * | 8/1997 | Lamond et al. ................... 607/5 |
| 5,868,790 A | 2/1999 | Vincent et al. |
| 6,556,864 B1 | 4/2003 | Picardo et al. |
| 6,558,381 B2 * | 5/2003 | Ingle et al. ...................... 606/41 |
| 2003/0181950 A1 | 9/2003 | Powers et al. |
| 2004/0015194 A1 * | 1/2004 | Ransbury et al. ............... 607/10 |

FOREIGN PATENT DOCUMENTS

WO     2004064919 A     8/2004

* cited by examiner

*Primary Examiner* — Carl H Layno
*Assistant Examiner* — Pamela M Bays
(74) *Attorney, Agent, or Firm* — W. Brinton Yorks, Jr.

(57) ABSTRACT

An automatic external defibrillator is shipped from the manufacturer with the battery installed in the battery compartment of the AED. During shipment a removable tab is located between a battery terminal and an electrical contact inside the battery compartment. Upon receipt of the AED the user pulls the tab to remove it from the battery compartment. This completes the circuit between the AED and its battery and the AED begins a self-test. A packaging panel covers the controls of the AED to prevent actuation of controls during the self-test. The packaging panel includes instructions for setup of the AED including indication of a control to actuate during or at the conclusion of the self-test.

18 Claims, 6 Drawing Sheets

OTC AUTOMATIC EXTERNAL DEFIBRILLATOR WITH QUICK INSTALL BATTERY

This application claims the benefit of Provisional U.S. patent application Ser. No. 60/639,476, filed Dec. 27, 2004 and Provisional U.S. patent application Ser. No. 60/689,115, filed Jun. 8, 2005.

FIELD OF THE INVENTION

This invention relates to automatic external defibrillators (AEDs) and, in particular, to AEDs which can be sold to individuals over the counter (OTC) without a prescription.

BACKGROUND OF THE INVENTION

Automatic external defibrillators have been in use for a number of years to treat individuals stricken with sudden cardiac arrest, one of the largest causes of death in the United States. Sudden cardiac arrest (SCA) most often occurs without warning, striking people with no previously recognized symptoms of heart disease. It is estimated that more than 1000 people per day are victims of sudden cardiac arrest in the United States alone. SCA results when the electrical component of the heart no longer functions properly causing an abnormal sinus rhythm. One such abnormal sinus rhythm, ventricular fibrillation (VF), is caused by abnormal and very fast electrical activity in the heart. As a result, the heart fails to adequately pump blood through the body. VF may be treated by applying an electric shock to a patient's heart through the use of a defibrillator. The shock clears the heart of abnormal electrical activity (in a process called "defibrillation") by producing a momentary asystole and providing an opportunity for the heart's natural pacemaker areas to restore normal rhythmic function. When delivered external to the patient, these electrical pulses are high energy pulses, typically in the range of 30 to 360 Joules of energy.

Defibrillators have undergone an evolution over the past decade. Originally defibrillators were manual devices requiring both medical and technical expertise to operate. A physician would carefully set the controls of the defibrillator to apply a shock which diagnosis of the patient or experience with other patients in similar conditions indicated to be most likely to be effective. Following many years of experience with manual defibrillators and motivated by advances in microprocessing and signal analysis, defibrillators have become more automated to the point where a two-pad electrode attached to a patient's chest can detect and diagnose VF and deliver an appropriate shock through the chest wall. However such automated defibrillators continued to be prescription devices used by medical professionals or under the auspices of a controlled emergency response program as described in U.S. Pat. No. 6,694,299. In the final months of 2004 AEDs have reached a level of sophistication and reliability which now enables them to be sold to laypersons without prescription, as over-the-counter (OTC) medical devices. AEDs may now be sold through retail channels (stores, websites, catalogs) and purchased by anyone for use at home in the event of a sudden cardiac arrest emergency.

Prescription AEDs given to patients by physicians or used in institutions such as hospitals, airports, office buildings, and emergency response organizations are initially handled by trained medical professionals. When these medical professionals receive an AED the electronic unit is boxed together with electrode pads, instruction guides, and a battery pack. The AED and its accessories are assembled by the medical professional including the installation of the battery pack into the battery compartment of the AED. The AED is then powered up and performs a self-test. An OTC AED, on the other hand, is purchased and initially handled by a consumer, and needs no intervention by a medical professional. This means that the consumer can face the task of assembling the OTC AED and getting it ready for use without any professional help. This is a prospect of considerable concern, for it is essential that the OTC AED be fully operational when it is needed to save a life. One solution to this dilemma is to sell the OTC AED to the consumer in a fully assembled state. However a fully operational AED will generally be performing periodic self-testing to continuously assure its operability. This presents the prospect of an OTC AED alarming during shipment to the retail outlet if the self-testing identifies a problem that needs to be addressed. An OTC AED alarming in a shipping container in an airport or other transit facility or carrier could be very disruptive to the facility or carrier personnel who are unaware of its presence. This makes shipment of fully operational AEDs by common carrier inadvisable. It is desirable, then, for an OTC AED to be easy to prepare for use by a layperson without professional medical guidance.

SUMMARY OF THE INVENTION

In accordance with the principles of the present invention an AED is packaged with its battery installed in the AED unit but not electrically engaged with the AED. This means that there is no hazard from the OTC alarming during transit as the AED is not powered up. Upon initial set-up of the AED the purchaser or user performs a simple act to electrically connect the battery to the AED. In an illustrated embodiment this act comprises removing an insulator separating a battery terminal from its contact in the AED. This initial connection of the battery will enable an immediate self-test, at which point the AED is fully ready for use.

DETAILED DESCRIPTION

Figure 1:
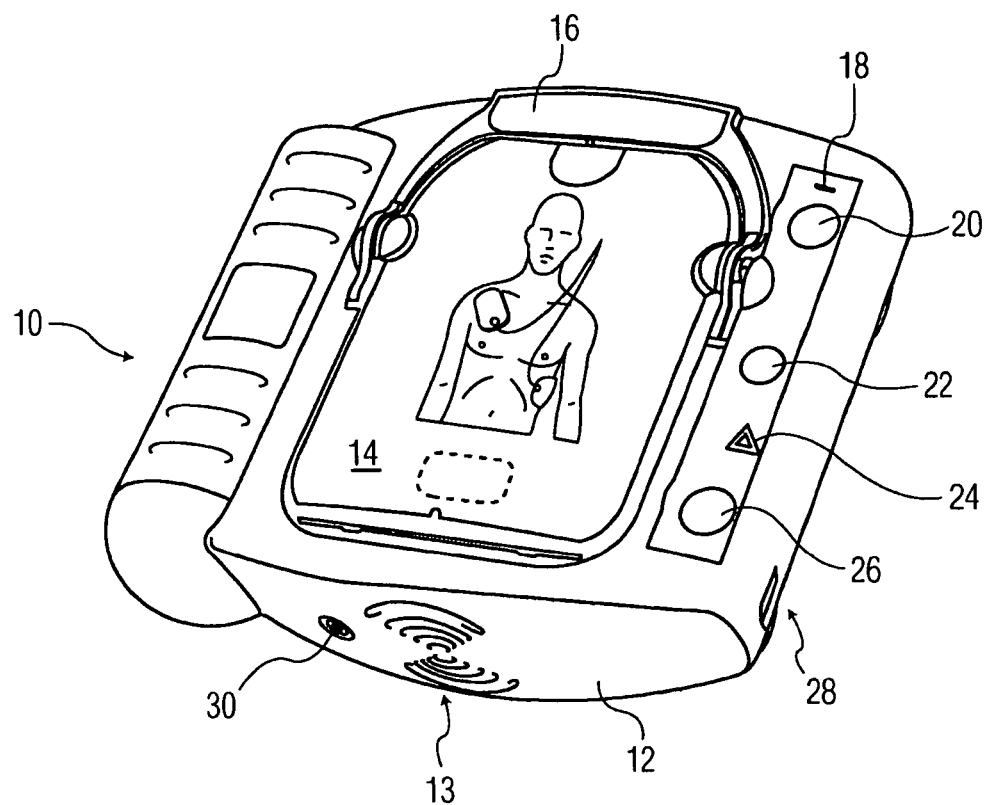
FIG. 1 illustrates a top perspective view of an OTC automatic external defibrillator.

Referring first to FIG. 1, an OTC AED 10 is shown in a top perspective view. The OTC AED 10 is housed in a rugged polymeric case 12 which protects the electronic circuitry inside the case and also protects the layperson user from shocks. In this embodiment the case is colored a distinctive color which readily identifies the OTC AED to the layperson user, such as red, yellow, orange, green, blue, black, or combinations thereof. Other suitable distinctive colors are light green, silver gray, and various shades of white or off-white. Combinations of the aforementioned colors also provide distinctive colorings to the layperson user such as yellow/black, yellow/blue, yellow/white gold/black, blue/silver, yellow/blue/black, and blue/white/black. Other distinctive colors include the yellows, oranges and reds often used for traffic signs and signals. It is important in the home environment that the OTC AED be marked by a prominent color or colors so as to be immediately recognized by a potential rescuer in the event of a home cardiac emergency. Unlike airports and public facilities where AEDs are generally mounted in distinctive locations such as on walls in high traffic areas and with signage to mark and indicate their locations, an OTC AED may be placed anywhere in the home. Since a home OTC AED may go an extended period of time without use, it may be stored in a location lacking prominence such as in a closet or drawer. Accordingly it is very important for the OTC AED to bear a distinctive color as this may be the primary means by which a rescuer can quickly locate the OTC AED in the home during an emergency. The OTC AED may be stored when not in use in a carrying case which may be a distinctive color such as red, black, navy blue, or blue/yellow color.

Attached to the case 12 by electrical leads are a pair of electrode pads. In the embodiment of FIG. 1 the electrode pads are in a sealed airtight cartridge 14 located in a recess on the top side of the OTC AED 10. The electrode pads are accessed for use by pulling up on a handle 16 which allows removal of a plastic cover over the electrode pads. A small ready light 18 informs the user of the readiness of the OTC AED. In this embodiment the ready light blinks after the OTC AED has been properly set up and is ready for use. The ready light is on constantly when the OTC AED is in use, and the ready light is off when the OTC AED needs attention.

Below the ready light is an on/off button 20. The on/off button is pressed to turn on the OTC AED for use. To turn off the OTC AED a user holds the on/off button down for one second or more. An information button 22 flashes when information is available for the user. The user depresses the information button to access the available information. A caution light 24 blinks when the OTC AED is acquiring heartbeat information from the patient and lights continuously when a shock is advised, alerting the rescuer and others that no one should be touching the patient during these times. Interaction with the patient while the heart signal is being acquired can introduce unwanted artifacts into the detected ECG signal. A shock button 26 is depressed to deliver a shock after the OTC AED informs the rescuer that a shock is advised. An infrared port 28 on the side of the OTC AED is used to transfer data between the OTC AED and a computer. This data port find used after a patient has been rescued and a physician desires to have the OTC AED event data downloaded to his or her computer for detailed analysis.

A speaker 13 provides voice instructions to a rescuer to guide the rescuer through the use of the OTC AED to treat a patient. A beeper 30 is provided which "chirps" when the OTC AED needs attention such as electrode pad replacement or a new battery.

Figure 2:
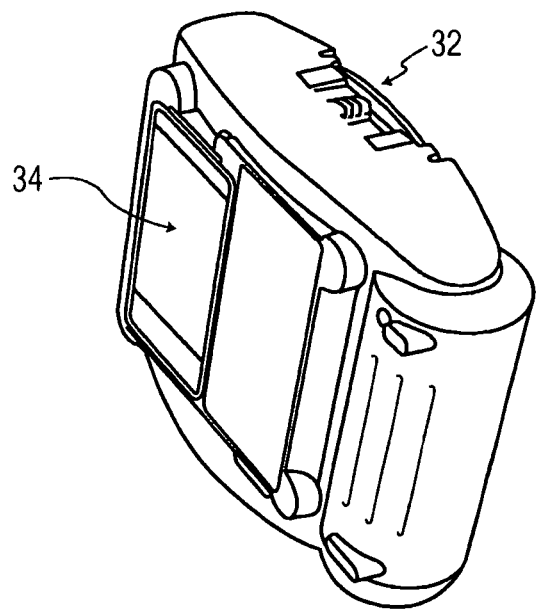
FIG. 2 illustrates a bottom perspective view of the OTC automatic external defibrillator of FIG. 1.

FIG. 2 illustrates another view of the OTC AED 10 in which a cartridge latch 32 is seen on the upper end of the OTC AED. When this latch is pushed to the right the electrode pad cartridge is released from its recess in the OTC AED case 12. The cartridge latch 32 is used when an electrode pad cartridge is to be replaced or exchanged for a training pad set for training on the OTC AED. On the back of the OTC AED case is a battery compartment which houses a battery 34 that powers the OTC AED. In this embodiment the battery 34 is a disposable battery. When the battery 34 becomes discharged, generally after about four years in the readiness state, it is replaced with a fresh battery.

In this embodiment the OTC AED contains self-test circuitry which automatically monitors the state of various parts of the OTC AED on a regular basis. Self-test circuitry is very important for an OTC AED because it cannot be expected that purchasers of the OTC AED will adhere to any formal maintenance schedule for the OTC AED. One component that is self-tested in this embodiment is the battery and another is the electrode pad set. The electrode pads include an adhesive gel which adheres the electrodes to the patient and provides good electrical conductivity with the patient. This adhesive gel is hydrophilic and over time can become subject to desiccation which reduces the effectiveness of the pads. In the hospital setting or the medical emergency responder setting electrode pads are generally used in a relatively short time-frame and desiccation is often not a problem. In addition, these medical professionals are generally more cognizant of the need for attention to expiration dates and other maintenance to their medical equipment. Electrode pads for the prescription defibrillators used by these medical professionals are often not connected to the defibrillator until the defibrillator is to be used and thus cannot be tested by the AED prior to use. Organizations such as airports and office buildings which have deployed defibrillators generally do so under the direction of a medical officer who oversees a maintenance program for the defibrillators. Prescription defibrillators are dispensed under the watchful eye of the prescribing physician who will be mindful of needed periodic maintenance such as electrode pad replacement. In the home environment where the OTC AED is not under the care of a prescribing physician it is to be expected that an OTC AED may sit in readiness for the full two-year anticipated lifetime of a typical electrode pad set without being inspected or used. Accordingly, in one embodiment of the present invention the electrode pads are normally electrically connected to the OTC electronic unit 10 and its self-test circuitry while the OTC AED is in the readiness state. With an electrode pad cartridge this can be done by embedding conductors in the wall of the cartridge. The electrode pad leads inside the cartridge are connected to these conductors, which enables electrical connectivity to the exterior of an air-tight sealed cartridge. The cartridge conductors engage mating conductors in the recess of the OTC AED case, thereby putting the electrode pads into electrical communication with the OTC AED self-test circuitry. This permits the electrode pads to be automatically tested by the OTC AED on a periodic basis by measuring the impedance through the circuit which includes electrical leads to each electrode pad, the conductor of each electrode, and the conductive gel on each electrode conductor. If the self-testing determines that the electrode pads have dried out or suffered some other detected deterioration as by an impedance measurement which is outside an expected impedance range, the user is alerted to replace the pads by the chirping of the beeper 30 and the absence of the ready light 18. Further details of electrode self-testing may be found in U.S. Pat. No. 6,694,193, the contents of which are incorporated herein by reference.

When defibrillators of the present invention are shipped to retailers or purchasers the units are shipped without the battery being installed. This prevents the possibility of the AED beeping or alarming during shipment or storage when it may be in a container with a common carrier, on an airplane or truck, or in an airport or other transit facility. A container in an airport which suddenly started to emit an audible alert could be very alarming to airport personnel. Thus, AEDs are conventionally not shipped with the batteries installed because of the possibility that a self-test performed during shipment could detect an error condition, causing the defibrillator to issue its audible alerts for maintenance during shipment, a situation to be avoided for obvious reasons such as airline safety. There is also the possibility of inadvertent activation and the resultant hazard if the high voltage circuitry begins to charge the defibrillator capacitor to its usual level of hundreds or thousands of volts. After the defibrillator is received by the purchaser, the first action of the medical professional is to install the battery in the defibrillator, at which point the defibrillator usually performs a self-test known as a "battery insertion test." This process begins the setup of the defibrillator, which may require periodic intervention by the medical professional before setup is complete.

Figure 3:
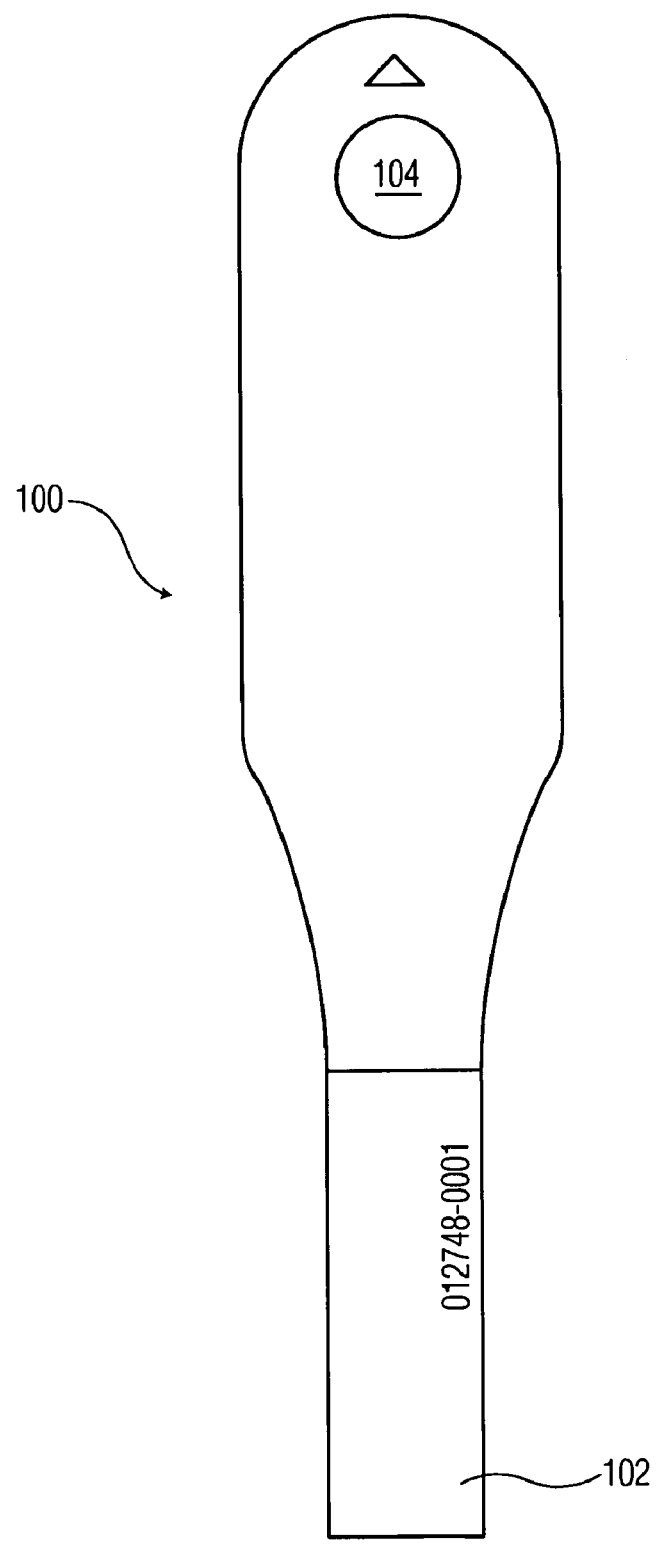
FIG. 3 illustrates a pull tab which connects the battery to an OTC AED and initiates the setup procedure.

As mentioned above, it is important that an OTC AED be promptly set up when the layperson purchaser takes it home. Furthermore, it is desirable to make setup as simple as possible for the nonmedical layperson. In accordance with the principles of the present invention setup of the OTC AED is simplified by providing the OTC AED with its battery already installed in its battery compartment, alleviating the layperson of this task. However, to prevent inadvertent alarming or charging of the high voltage circuitry and capacitor during shipment, the battery circuit is broken by a nonconductive pull tab 100 during shipment as illustrated in FIG. 3. The distal end 102 of the pull tab 100 is disposed in the battery circuit such as between one battery terminal and its contact on the OTC AED. In a constructed embodiment the battery has four terminals which engage four contacts on the OTC AED, and the distal end 102 is disposed between all four terminals and contacts, completely isolating the battery from the high voltage circuitry of the OTC AED. The pull tab 100 may be made of a sheet of nonconductive material such as paper or cardboard. In a constructed embodiment the pull tab 100 is made of a thin polymeric sheet which is tough enough not to tear when a finger is inserted in the hole 104 in the proximal end of the pull tab and the pull tab is pulled from between the battery terminals and OTC AED contacts. The thin sheet enables the battery to be latched in place in the battery compartment while the pull tab is in place during shipment. The polymeric material also gives the pull tab a resilient property. During shipment in a constructed embodiment the pull tab is folded over the top of the OTC AED when the OTC AED is in the carrying case, and the case is closed. When the case is opened for the first time the resilient pull tab pops up, immediately informing the layperson what is to be done first. The pull tab may be labeled with instructions at its proximal end such as "pull" or "remove first", or it may be labeled with a graphic such as an arrow pointing up (shown above hole 104), or it may be left unlabeled, with the pop-up characteristic speaking for itself.

It will be appreciated that it is not necessary for the pull tab to pop up when the OTC AED is initially accessed as described above. In another embodiment the pull tab may be prominently positioned so that it is one of the first items seen by the new purchaser when opening the OTC AED package. It is sufficient in most embodiments if the purchaser recognizes the pull tab and understands that it is to be removed.

While the installed battery is a benefit because it alleviates the layperson purchaser of this task, it is also an advantage because the OTC AED packaging does not have to accommodate a separate battery pack and thus can be made smaller. In a constructed embodiment the OTC AED with battery installed and in its carrying case 44 measured 3½" by 8" by 9", a total of 252 in³, and was packed in packaging measuring 6.5" by 8.375" by 10.5", a total of 572 in³. The OTC AED and case thus occupy 44% of the packaging volume.

Figure 4:
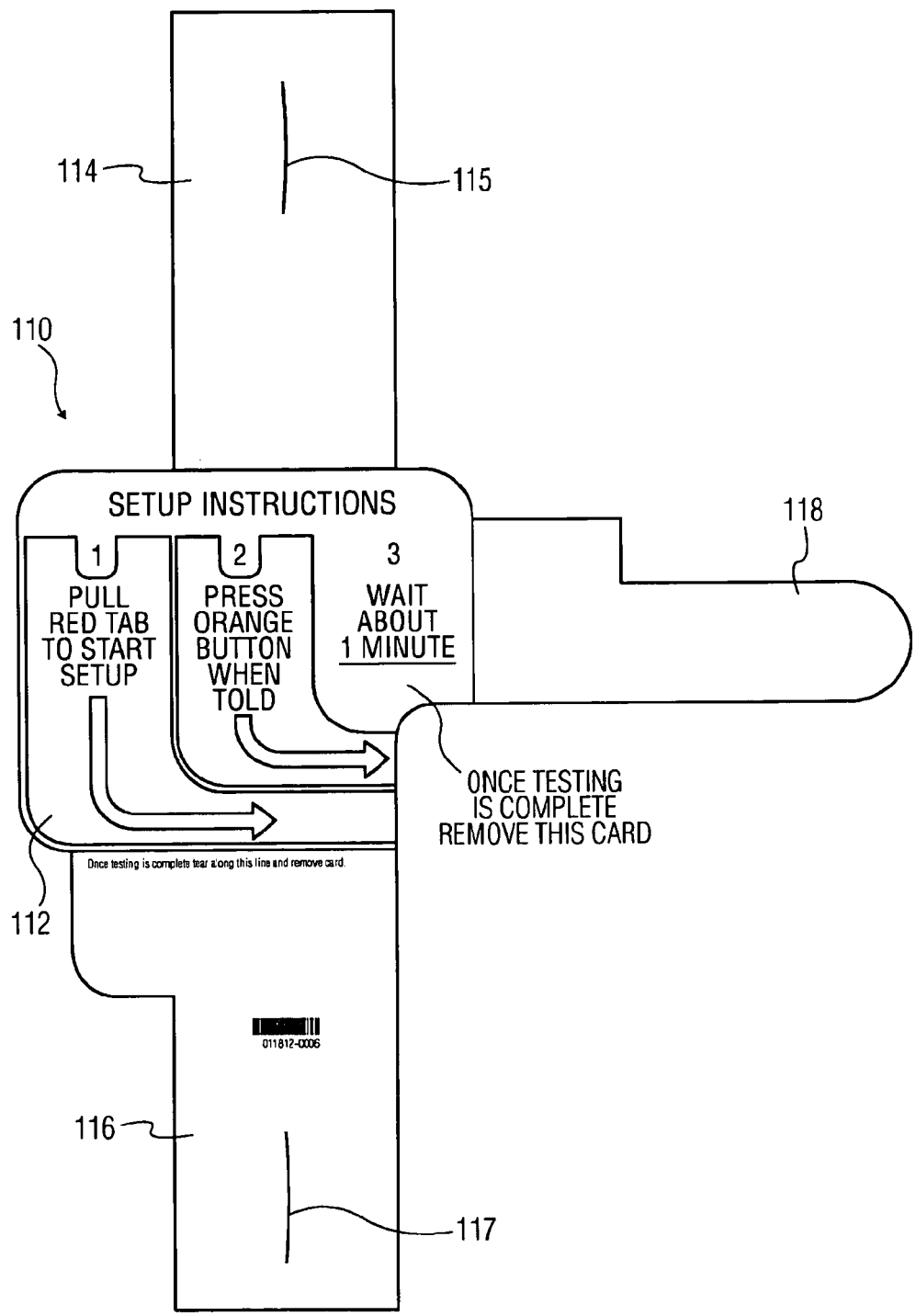
FIGS. 4 and 5 illustrate a shipping cover which facilitates the setup procedure.
Figure 5:
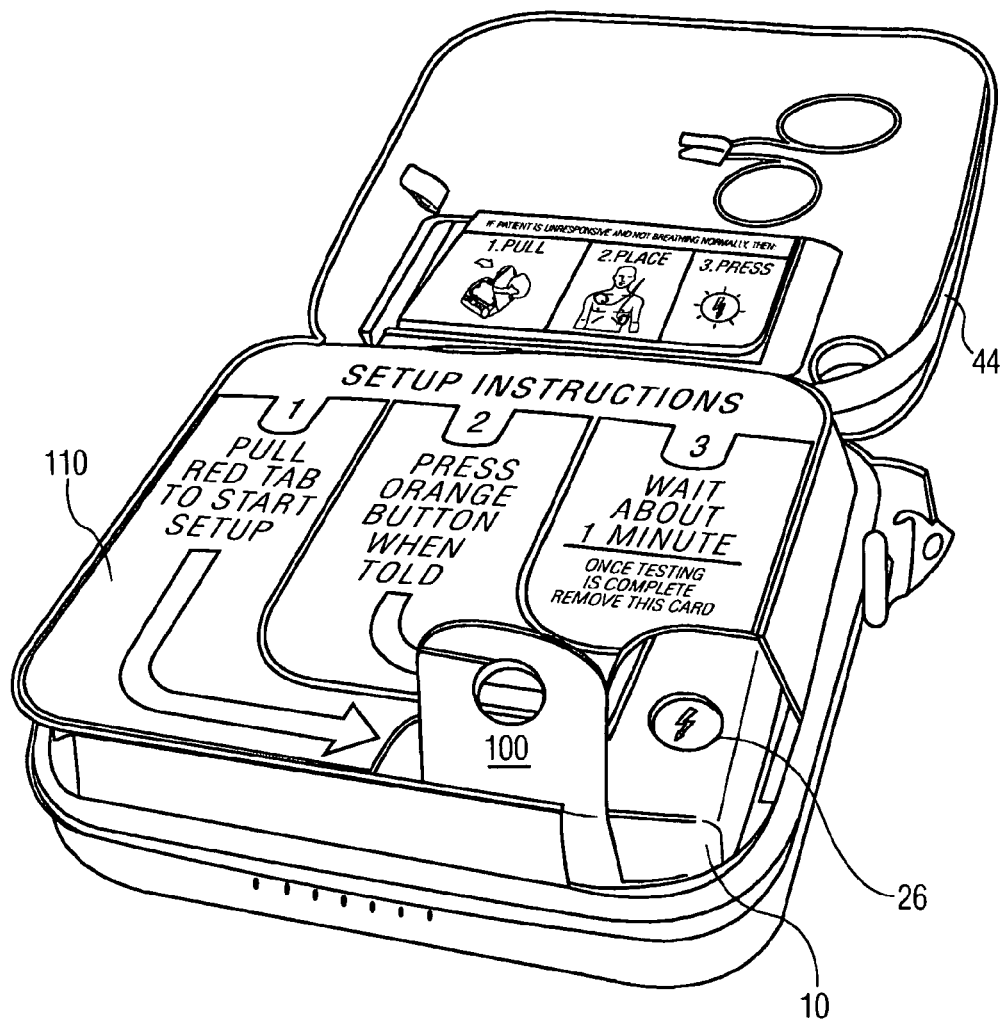

In accordance with a further aspect of the present invention, the top of the OTC AED is covered with a sheet 110 that obscures from the user certain ones of the controls of the OTC AED, seen in FIG. 1, except for those that are to be used to set up the OTC AED. An embodiment of a sheet 110 is shown in FIG. 4, comprising the top area 112 which covers the top of the OTC AED and contains three instructions: pull the red tab 100 to start the automated setup process; press the orange button indicated by the second arrow when prompted by an audible instruction; and wait until an audible prompt announces that the setup is complete. Two tabs 114 and 116 extend from the top area 112 and fold under the OTC AED, where they are engaged through slits 115 and 117 by a third tab 118, retaining the cover in place around the OTC AED. In a constructed embodiment this sheet comprises removable cardboard packing that covers all but the shock button 26 on the top of the OTC AED 10 as shown in FIG. 5.

When the new purchaser opens the carrying case 44 for the first time, the pull tab 100 pops up and the purchaser responds by pulling the tab, connecting the battery terminals to the contacts of the OTC AED. The OTC AED will then immediately commence its battery insertion test, and the audible prompts may announce to the purchaser that testing is underway. During or at the conclusion of the battery insertion test, the purchaser is asked to respond by pressing the shock button 26. At this point no other controls are visible to the purchaser by reason of the cover sheet 110 covering the top of the OTC AED controls except for the shock button. The cover sheet also inhibits the purchaser from pressing any other buttons on the OTC AED while the battery insertion test is in progress. In the illustrated embodiment the cover sheet 110 also obscures the pull handle for the pads cartridge as it is not necessary for the purchaser to pull this handle during setup. At the conclusion of the battery insertion test, no additional user intervention is needed. The purchaser can dispose of the pull tab 100 and the cover sheet 110 and the OTC AED is set up and ready for use in a cardiac emergency.

Purchasers of OTC AEDs may have different individual requirements for storing and training for use of the OTC AED. In accordance with a further aspect of the present invention an OTC AED is sold in multiple accessory configurations. In the most basic configuration the OTC AED is sold in packaging containing only the OTC AED (and carrying case if it has one) and the literature kit for the unit. A typical literature kit includes instructions for setup and use, warranty information, support program reply card as described below, training video, and possibly other information. In the "training" configuration the packaging contains the OTC AED (and case, if appropriate), the literature kit, and a package of training pads. The training pads are used with the OTC AED when the user wants to train himself or others in the use of the OTC AED. In the "emergency healthcare" configuration the packaging contains the items of the training configuration and a first aid kit which the purchaser may also use for home medical emergencies. In the "wall mount" configuration the packaging contains all of the items of the emergency healthcare configuration and a wall mount for mounting the OTC AED on a wall. It will be appreciated that in a given embodiment different mixes of these items will be included and other packaging configurations can be arranged. For example, a configuration of the OTC AED, carrying case, literature kit, training pads and wall mount may be desirable for certain users who already have a first aid kit.

Figure 6:
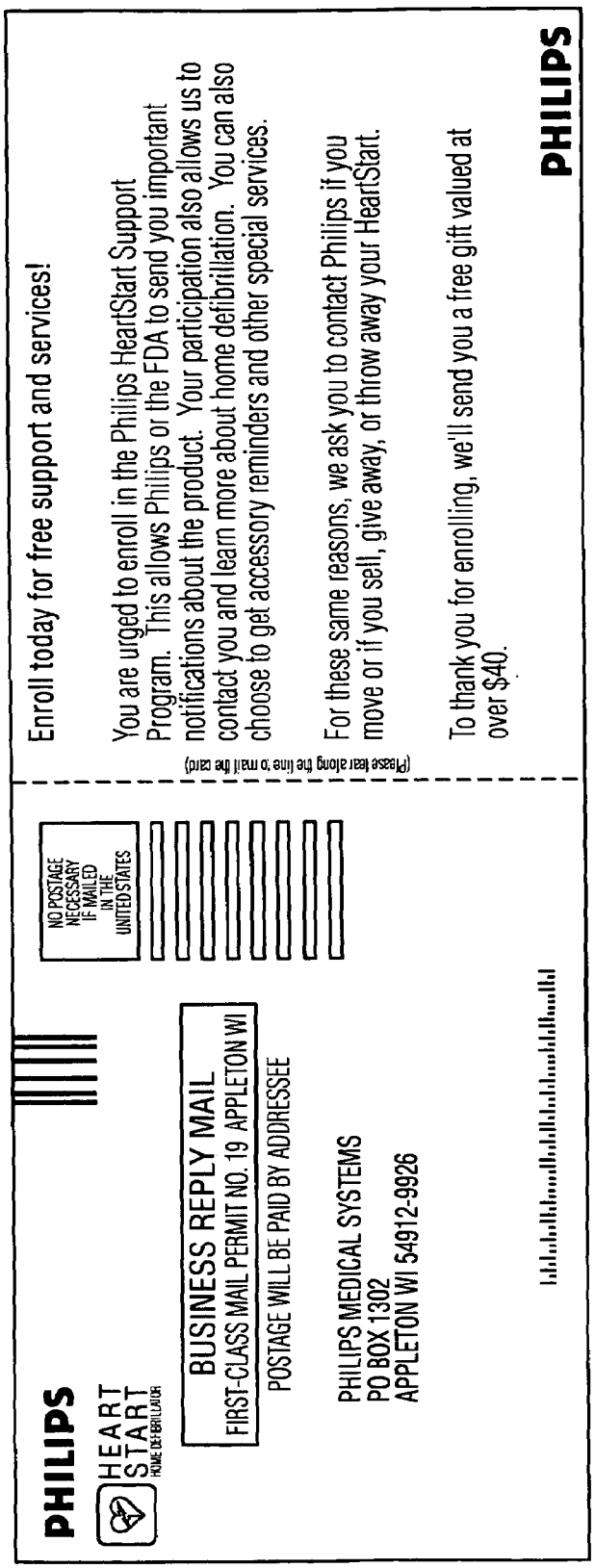
FIGS. 6 and 7 illustrate the front and back of an OTC AED support program enrollment card.
Figure 7:

As previously mentioned it is to be anticipated that the consumer purchaser of an OTC AED will be unmindful of any maintenance needs of the OTC AED while it is in its standby state. In accordance with a further aspect of the present invention, a support program for an OTC AED is provided by multiple communications with the purchaser of the OTC AED. To facilitate these communications a mail-in support program card is included in the packaging of the OTC AED, an example of which is shown in FIGS. 6 and 7. The support program card elicits the purchaser's contact information such as mailing address and telephone number and has a space for the serial number of the OTC AED. The card may also request that the manufacturer be notified if ownership of the OTC AED is transferred to someone else or if the OTC AED is no longer in service. It may also provide a space where the purchaser can state the kind of support desired, such as reminders when the battery or pads need replacing or updates on home defibrillation. In the illustrated embodiment the support program card comes with detachable instructions and offers an incentive if the card is returned as requested.

When the new owner enrolls in the support program and provides the necessary contact information, periodic contacts with the owner may then be conducted. For example, a first such communication can be a letter mailed to the enrolled owner of the OTC AED after approximately the first year of ownership. Such a letter may remind the owner to check the battery and pads of the OTC AED to see if they need replacing, and to set up the OTC AED if that has not already been done. The letter may also offer training opportunities to the purchaser such as reviewing a training video. The letter may also solicit information such as whether the OTC AED was used in an emergency during the past year and whether its ownership or possession have been transferred to another person. A second such communication may occur after two years of ownership, which is approximately the time that pads need replacing. In addition to the foregoing, the letter may remind the owner that the pads of the OTC AED need replacing and may include contact information and an incentive to do so. A similar communication may be sent at the later date when the battery is scheduled for replacement. Such a support program can help keep a potential home rescuer trained to use the OTC AED, can help keep the OTC AED properly maintained, and provides a means to follow ownership of the OTC AED through successive owners so that such services can continue with whomever owns the OTC AED. The contact information also provides a means for the manufacturer to contact the owner if upgrades or improvements or critical information concerning the OTC AED become available in the future.

What is claimed is:

1. An automatic external defibrillator which is packaged for automated setup prior to use in a cardiac emergency comprising:
    an automatic external defibrillator electronic unit including high voltage circuitry and a battery compartment having an electrical contact for connection to a battery;
    a battery, located in the battery compartment, and having a battery terminal; and
    a disposable circuit interrupter, located in the circuit between the battery terminal and the electrical contact when the automatic external defibrillator is packaged prior to use, which breaks the electrical circuit between the battery terminal and the electrical contact until a user puts the automatic external defibrillator into service,
    wherein the electronic unit is activated by the removal of the disposable circuit interrupter to perform an automated setup process of the automatic external defibrillator which readies the automatic external defibrillator for use prior to a cardiac emergency.

2. The automatic external defibrillator of claim 1, wherein the circuit interrupter comprises a nonconductive material located between the electrical contact and the battery terminal.

3. The automatic external defibrillator of claim 2, wherein the nonconductive material comprises a paper or cardboard material.

4. The automatic external defibrillator of claim 2, wherein the nonconductive material comprises a polymeric material.

5. The automatic external defibrillator of claim 2, wherein the circuit interrupter comprises an elongated sheet having a first end located between the electrical contact and the battery terminal and a second end suitable for being grasped by a user to remove the first end from between the electrical contact and the battery terminal.

6. The automatic external defibrillator of claim 5, wherein the elongated sheet further includes an aperture at the second end.

7. The automatic external defibrillator of claim 1, wherein the electronic unit further includes a self-test circuit, wherein the self-test circuit performs a self-test after the circuit interrupter is removed to restore the circuit between the electrical contact and the battery terminal.

8. An automatic external defibrillator which is packaged prior to use comprising:
    an automatic external defibrillator electronic unit including high voltage circuitry, a self-test circuit, and a battery compartment having an electrical contact for connection to a battery;
    a battery located in the battery compartment when the automatic external defibrillator is shipped by the manufacturer, the battery having a battery terminal for engaging the electrical contact; and
    a removable circuit interrupter disposed between the battery terminal and the electrical contact, wherein removing the circuit interrupter activates both of the self-test circuit and the high voltage circuitry.

9. The automatic external defibrillator of claim 8, wherein the circuit interrupter prevents charging of the high voltage circuit during shipment of the automatic external defibrillator.

10. The automatic external defibrillator of claim 9, wherein the circuit interrupter prevents actuation of the self-test circuit during shipment of the automatic external defibrillator.

11. The automatic external defibrillator of claim 10, wherein the circuit interrupter is only used prior to the initial setup of the automatic external defibrillator.

12. The automatic external defibrillator of claim 10, wherein the circuit interrupter is removed during initial setup of the automatic external defibrillator.

13. An automatic external defibrillator which is packaged prior to use comprising:
    an automatic external defibrillator electronic unit including high voltage circuitry, self-test circuitry, and a control panel having a plurality of controls;
    a battery; and
    setup instruction packaging which is visible prior to an electrical actuation of the electronic unit and which obscures from the user certain ones of the controls except for those that are to be used to set up the defibrillator prior to use, the setup instruction packaging indicating at least one control of the control panel which is to be actuated to set up the automatic external defibrillator for use.

14. The automatic external defibrillator of claim 13, wherein the setup instruction packaging leaves the at least one control of the control panel unobscured and covers a second control of the control panel which is not to be used during setup of the automatic external defibrillator.

15. The automatic external defibrillator of claim 13 wherein actuation of the indicated control actuates a function associated with the operation of the self-test circuit.

16. A method of initializing an automatic external defibrillator for use comprising:
removing a disposable circuit interrupter to complete an electrical circuit between a battery and circuitry of the automatic external defibrillator and automatically initiate a self-test of the defibrillator; and
waiting for completion of a self-test by the automatic external defibrillator,
wherein the self-test is accompanied by at least one audible initializing instruction by the automatic external defibrillator.

17. The method of claim 16, further comprising actuating at least one control of the automatic external defibrillator which is associated with the self-test.

18. The method of claim 16, wherein removing the disposable circuit interrupter enables electrical connection of a terminal of the battery and a circuit contact of an electrical circuit of the automatic external defibrillator.

* * * * *